United States Patent [19]

Ebling et al.

[11] 4,098,274
[45] Jul. 4, 1978

[54] DIGITAL MEMORY WITH POWER OUTAGE AND MEMORY OVERLOAD LOGIC IN A DIALYSIS SYSTEM

[75] Inventors: Wendell Victor Ebling; David Allan Witsoe, both of Libertyville; Jan Soderstrom, Cary, all of Ill.

[73] Assignee: Baxter Travenol Laboratories, Inc., Deerfield, Ill.

[21] Appl. No.: 733,584

[22] Filed: Oct. 18, 1976

[51] Int. Cl.² .............................................. A61M 1/03
[52] U.S. Cl. ................................ 128/214 E; 210/90; 210/321 B; 128/DIG. 13; 128/2.05 D; 210/85
[58] Field of Search ................. 128/DIG. 1, DIG. 3, 128/DIG. 12, DIG. 13, 214 E, 214 B, 214 F, 214 R, 2.05 A, 2.05 R; 210/85, 90, 321 A, 321 B, 22 A, 22 C, 22 D; 23/258.5 R

[56] References Cited

U.S. PATENT DOCUMENTS

| | | | |
|---|---|---|---|
| 3,197,068 | 7/1965 | Corbin et al. | 128/214 E |
| 3,636,941 | 1/1972 | Guevrekian | 128/2.05 A |
| 3,655,095 | 3/1972 | Kienitz | 128/214 E |
| 3,731,680 | 5/1973 | Wright et al. | 128/214 F |
| 3,736,930 | 6/1973 | Georgi | 128/214 E |
| 3,814,082 | 6/1974 | Taylor | 128/2.05 R |
| 3,939,824 | 2/1976 | Arneson et al. | 128/2.05 A |
| 3,946,731 | 3/1976 | Lichtenstein | 23/258.5 R |
| 4,011,860 | 3/1977 | Lee | 128/2.05 A |

*Primary Examiner*—Robert W. Michell
*Assistant Examiner*—Francis J. Jaworski
*Attorney, Agent, or Firm*—Paul C. Flattery; Gerald S. Geren

[57] ABSTRACT

There is disclosed herein a blood pressure alarm system for use in a dialysis machine whereby alarms may be activated, and a blood pump deactivated if the actual blood pressure increases above or decreases below predetermined levels. The levels are determined by setting a particular blood pressure point and setting the amount by which the pressure can vary above and below the set point. A memory is provided for storing the set point and preventing variation of the set point with time. The dialysis machine and alarm system can malfunction under certain conditions and protection circuitry operates the alarms if a malfunction occurs.

15 Claims, 7 Drawing Figures

DIGITAL MEMORY WITH POWER OUTAGE AND MEMORY OVERLOAD LOGIC IN A DIALYSIS SYSTEM

BACKGROUND OF THE INVENTION

This invention relates to dialysis machines of the type used in artificial kidney systems, and more particularly, to a blood pressure alarm system for use therein.

In a dialysis machine water and concentrate are mixed to provide dialysis solution which is delivered to a dialyzer through which both blood an dialysis solution flow on opposite sides of a semipermeable membrane. Waste products from the blood pass through the membrane into the dialysis solution for disposal. Normally dialysis takes approximately 4–6 hours.

Dialysis machines are equipped with both arterial and venous blood pressure alarm systems for activating an alarm and for deactivating a blood pump in the extracorporeal blood circuit in the event that the blood pressure in the blood circuit exceeds or falls below predetermined values. This is sometimes referred to as an alarm window. Proper monitoring of both the arterial and venous pressure is important since failure or errors in monitoring can result in blood loss from the patient.

One alarm monitoring system provides for alarm conditions when the blood pressure varies by more than ± 50 mm/Hg from an adjustable and manually set pressure point. The pressure selector is a knob having an indicating arrow which is set with respect to pressure indicating markings on a face plate. A meter is provided which displays the actual pressure but not the selected pressure. A comparator is provided to compare actual pressure against the set point ± 50 mm/Hg. This system had disadvantages in that: (1) the nurse could err in setting the reference point; (2) the face plate/knob relationship could be off which would result in an erroneously selected reference point; and (3) the machine characteristics could vary which would result in an erroneous reference point.

In an effort to overcome these problems, an unmarked plunger-type knob was provided which cooperates with the meter for the setting of the reference point. With the knob in the out position, the meter displays actual blood pressure and, when pushed to the in position, the meter is engaged and the reference point can be selected against the meter scale. The alarm is still set ± 50 mm/Hg above and below the reference point. With this system the errors due to knob mounting and machine error are eliminated and the internal pressure transducer and alarm set knob referenced against the same meter. However, this system is inconvenient to operate since the knob has to be pushed in and out to set while watching the meter. Furthermore, the variability about the reference point could not be controlled.

In a third generation machine, provision is made to set the reference point using the pressure produced when the dialysis machine is operating and the patient's condition has stabilized. By moving a slide switch from a set-up mode to an operate mode, the reference point is set into the machine. This eliminates the need for the plunger-type knob, and a second slide control is provided by which the variability about the reference point can be adjusted between ± 10 and ±100 mm/Hg. In this system a memory is provided which stores the reference point. The memory is essentially a capacitor, and the charge on the capacitor is updated every 5 minutes during dialysis by comparison against the actual blood pressure at that point in time, so long as no alarm condition had been met. The blood pressure at 5 minutes, 10 minutes, etc., can be different than the desired reference point. It should be noted that the variability is set against the memory point. Thus, changes in the charge on the capacitor could result in changes in the alarm conditions which would be undesirable.

In machines such as the third generation machine noted, a meter is provided to enable visual observation of the patient's blood pressure and the pressure set point. The meter can be adjusted in order to provide a full-scale deflection for a particular selected transducer pressure. During or after the meter is adjusted to give full-scale deflection for the specified pressure, if the slide switch is moved to the set-up position, then returned to its operate position, the reference point stored in the memory will be equivalent to a full-scale meter reading. If the slide control which provides variability about the reference point is adjusted to provide ± 55 mm/Hg, the alarm will not operate until the blood pressure sensed is substantially in excess of that capable of being read on the meter.

In the machine noted and in any machine with a memory, the memory employed has a finite capacity. It is possible, during the set-up mode, to couple a signal to the memory which is in excess of the memory capacity. In such a circumstance, the memory may accept no signal for storage, it may accept only a part of the received signal, or it may accept a signal level which is totally unrelated to the reference point which should be stored in the memory. It is desirable to be able to ascertain when such a condition occurs and prohibit operation of the machine until the memory has been stabilized with the proper reference point stored therein.

In like manner, loss of supply potential at the memory for a specific time period will cause the release of the contents stored therein. Should the supply voltage be reapplied shortly thereafter, the reference point stored in the memory may have no relationship to the reference point initially stored and desired. It is desirable to be able to ascertain when such a condition occurs and prohibit further operation of the machine until the proper reference point again has been stored in the memory.

It is therefore an object of this invention to provide a memory system for use in a blood pressure alarm system in a dialysis machine wherein the alarm conditions remain fixed relative to their initial settings with time.

It is another object of this invention to provide a dialysis machine with protection circuitry capable of detecting certain types of machine malfunctions and preventing further operation of said machine until the malfunctions have been corrected.

This and other objects will become apparent from the following description and appended claims.

SUMMARY OF THE INVENTION

There is provided by virtue of this invention an alarm circuit for use with a dialysis machine which alarms in response to blood pressure changes. A blood pressure sensing circuit in the alarm develops a pressure signal which varies in accordance with blood pressure. A memory receives the pressure signal and stores a signal corresponding to the pressure signal in a storage device. Control circuitry in the alarm is connected to the blood pressure sensing circuit and the memory. The control ciruitry operates in response to a difference between the pressure signal and memory signal to provide the noted alarm. A protection circuit responds to one of an off-scale meter reading, power reduction below a certain level for a specific time, or memory overload to operate for providing said alarm.

DETAILED DESCRIPTION OF THE PREFERRED EMBODIMENTS

Figure 1:
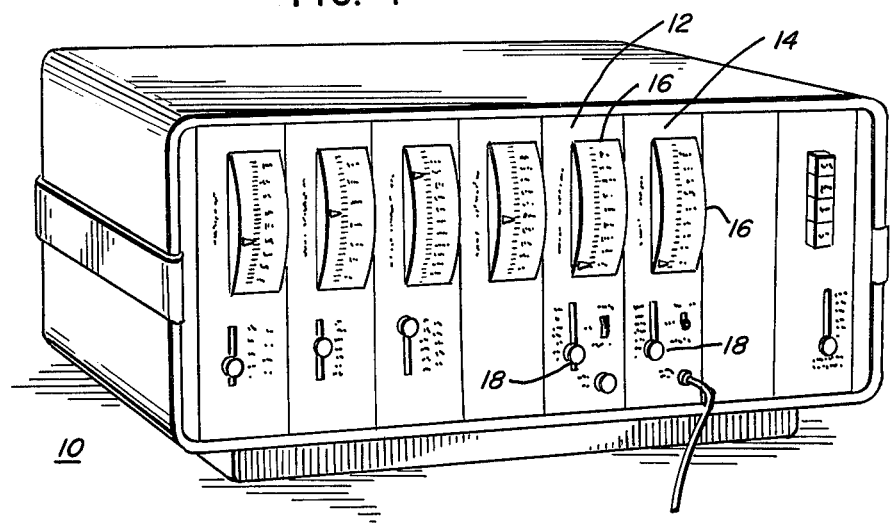
FIG. 1 is a perspective view of a dialysis machine of the type employing the alarm system of this invention.

Referring now to the drawings, a dialysis machine 10 generally includes a venous pressure module 12 and an arterial pressure module 14. Each module is substantially identical and includes a meter 16 for indicating blood pressure. A slide control 18 allows selection of an alarm window between ± 10 mm/Hg and ± 100 mm/Hg of the meter reading. A female connector 20 is provided for connection to a transducer to monitor blood pressure.

Since the arterial and venous modules are identical, the following description is in reference to the arterial module, it being understood that such description is applicable to the venous module.

Figure 2:
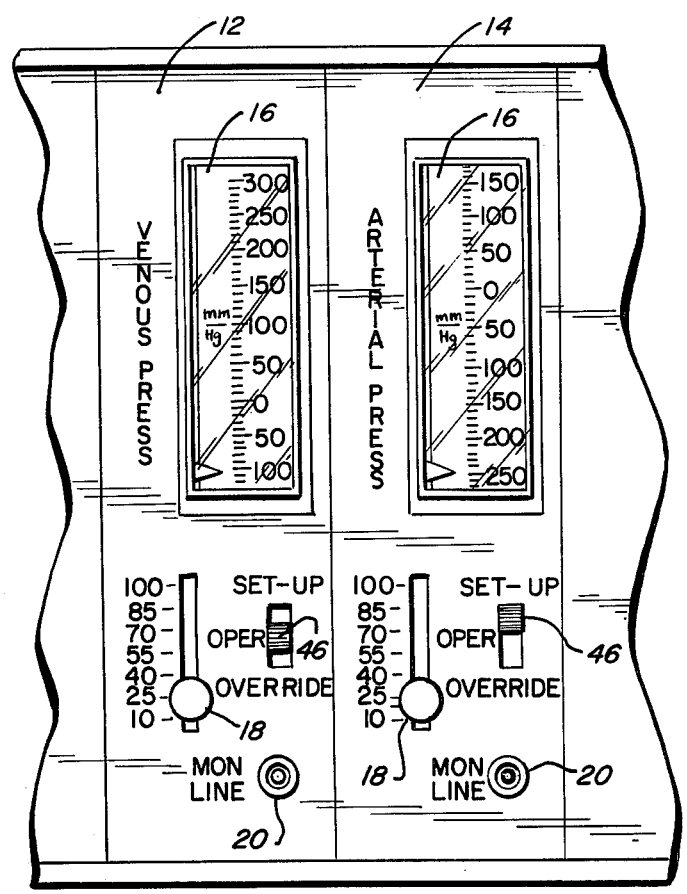
FIG. 2 is an enlarged view of a portion of the front panel of the machine showing the venous and arterial pressure controls.
Figure 3:
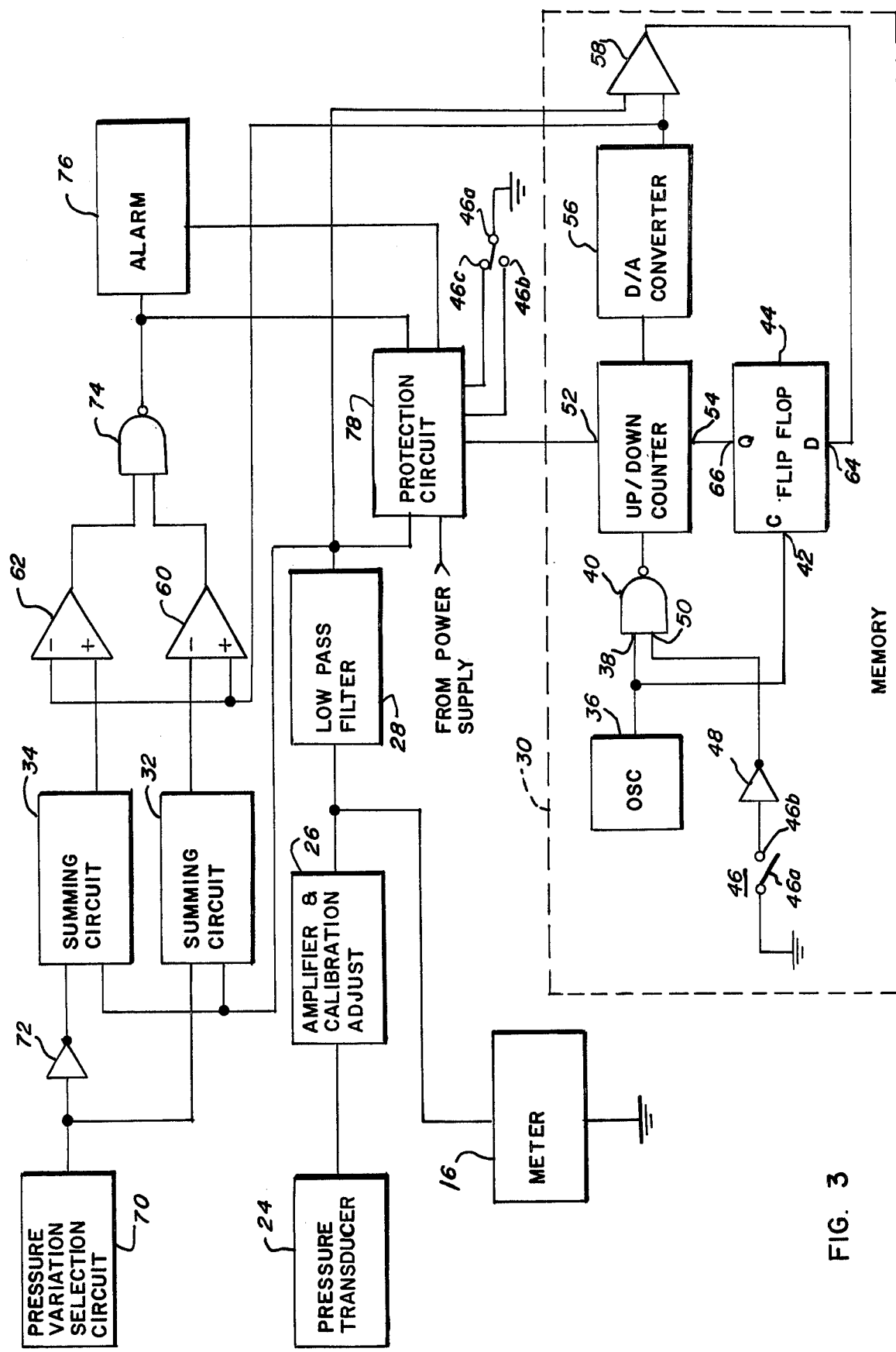
FIG. 3 is a block diagram of one embodiment of the alarm circuit of this invention.

Referring now to FIG. 3, the alarm circuit embodiment shown therein includes a pressure transducer 24 which attaches to the blood line between the patient and the dialysis machine. Pressure transducer 24 may be attached to the arterial blood line and then connected to the arterial module 14 by way of connector 20 (shown in FIG. 2). Pressure transducer 24 will sense the blood pressure in the attached line and develop a pressure voltage which varies in accordance with the sensed pressure level. This pressure voltage is coupled to an amplifier and calibration adjusting circuit 26.

Amplifier and calibration adjusting circuit 26 amplifies the received pressure voltage and couples the amplified voltage to meter 16, where it may be observed, and to low pass filter 28. The calibration adjusting circuit portion of amplifier and calibration adjusting circuit 26, in conjunction with meter 16, allows the manufacturer to calibrate the meter 16 against a pressure reference for any different pressure transducer 24 which may be utilized with machine 10.

The amplified pressure voltage coupled to low pass filter 28 is considered a DC signal even though it does vary in accordance with variations in pressure. The variation in pressure, however, are very slow variations and are non-periodic. Noise signals, such as may be developed by the ballasts in fluorescent lamps and as a result of a person's heart beats, may be sensed by pressure transducer 24 or coupled directly to the circuitry resulting in an AC-type signal added to the amplified DC pressure voltage. Low pass filter 28 operates to attenuate signals in excess of one-half cycle per second so that the DC amplified pressure voltage will pass through the low pass filter 28 with substantially no attenuation whereas the AC signals will be substantially attenuated. The amplified filtered pressure voltage from low pass filter 28 is coupled to a memory circuit 30, represented by dash lines, and to first and second summing circuits 32 and 34, respectively.

Memory circuit 30 includes an oscillator 36 which operates continuously to develop clock pulses which are coupled to one input 38 of NAND gate 40 and to the clock input 42 of a bistable multivibrator 44, more commonly known as a flip/flop.

A switch terminal 46b of switch 46 is connected to the input of inverter amplifier 48, the output of which is coupled to the second input 50 of NAND gate 40. In the set up position noted in FIG. 1, switch arm 46a connects ground potential to terminal 46b so that a high state signal appears at input 50. This allows the clock pulses developed by oscillator 36 to be coupled through NAND gate 40 to an up/down counter 52.

Up/down counter 52 either adds or subtracts each clock pulse received from a digital count stored therein in accordance with the state of an up/down control signal coupled to up/down control input 54. The digital count stored in up/down counter 52 is coupled to a digital to analog (D/A) converter 56 which develops an analog memory signal corresponding to the digital count signal in counter 52. The analog memory signal developed by D/A converter 56 is converted to a voltage and coupled to one input of a comparator 58 in memory 30 and to comparators 60 and 62.

In operation, dialysis machine 10 is connected to the patient, and pressure transducer 24 is connected to the arterial line. The signal developed by pressure transducer 24 is coupled through amplifier and calibration adjusting circuit 26 and low pass filter 28 so that an amplified filtered pressure voltage is coupled to one input of comparator 58. Assuming that the machine has just been initialized and no count is recorded in counter 52, the output voltage from converter 56 is less than the pressure voltage from low pass filter 28. Consequently, comparator 58 develops a high state or one level signal indicating that the pressure voltage is greater than the analog memory voltage at the output of converter 56. The high state signal is coupled to the D input 64 of flip/flop 44. Upon receipt of the next clock pulse at clock input 42, flip/flop 44 samples the high state signal at D input 64 and develops a high state signal at the Q output 66. The high state signal developed at the Q output 66 is coupled to up/down control input 54 of counter 52 causing counter 52 to count up adding each clock pulse received to the stored digital count.

It is to be understood that the above and following operation is described with respect to a pressure voltage greater than an analog memory voltage from converter 56. If the pressure voltage is less than the analog memory voltage, a low state signal is developed by comparator 58 and coupled to flip/flop 44. This results in a low state signal being coupled to the up/down control input 54 of counter 52 which sets counter 52 to count down, subtracting each clock pulse received from the stored digital count.

When machine operation is initialized, the switch 46 is in the set-up position connecting arm 46a to the terminal 46b. The set-up position connects ground potential to inverter amplifier 48 through switch 46. With ground potential at its input, a high state signal is coupled to input 50 of NAND gate 40 allowing clock pulses developed by oscillator 36 to be coupled to counter 52. Counter 52 is set to count up, as previously noted, adding each clock pulse received to the stored digital count, so that it begins counting and increasing the digital count stored therein. As the count increases, the analog memory voltage developed by D/A converter 56 increases. The analog memory voltage increases until it reaches and exceeds the pressure voltage coupled from low pass filter 28 to comparator 58. When the analog memory voltage exceeds the pressure voltage, the output of comparator 58 will change from a high to a low state. At the next clock pulse, the Q output 66 of flip/flop 44 will change from a high to low state, and counter 52 will begin to count donw, subtracting each clock pulse from the digital count stored therein. This will result in a slightly reduced voltage at the output of D/A converter 56. If the analog memory voltage now is below the pressure voltage, comparator 58 again will develop a high state signal at its output.

The hunting process, whereby the analog memory voltage goes slightly above and below the pressure voltage, continues as long as switch 46 remains in the set-up position. Because of the oscillator frequency, the hunting or switching occurs very rapidly. Because of the speed at which hunting occurs and the precision of comparator 58, the analog memory voltage developed differs only very slightly from the pressure voltage. When the patient's condition stabilizes, the technician, observing the patient and meter 16, recognizes that the patient's condition has stabilized and that the machine is operating properly as indicated by the blood line pressure shown on meter 16. The technician then moves switch 46 to the operate position, so that ground potential is removed from terminal 46b and clock pulses no longer can be coupled through NAND gate 40 to up/down counter 52. The count last stored is now held in counter 52, and a corresponding analog memory voltage is developed by D/A converter 56. The abovedescribed operation is similar to a tracking analog/digital servo system. Such a system operation in a memory to inhibit clock pulses has not previously been provided.

Slide control 18 shown in FIGS. 1 and 2 is a part of a pressure variation selection circuit 70 in FIG. 3. Pressure variation selection circuit 70 will develop an output voltage whose amplitude is adjustable to correspond to the desired blood pressure limits, adjustments being provided by slide control 18. In the embodiment shown, if a blood pressure variation of 10 mm/Hg above and below the selected blood pressure is desired, slide control 18 is moved to the line adjacent the number 10, and a very low voltage is developed by pressure variation selection circuit 70 corresponding to the pressure change of 10 mm/Hg above or below the preselected nominal pressure stored in digital form in memory 30. Should be limit of ± 100 mm/Hg be desired, slide control 18 is moved to the ± 100 line and the output voltage developed by pressure variation selection circuit 70 increases to represent the pressure variation of ± 100 mm/Hg. Pressure variation selection circuit 70 allows selection of an upper and lower limit, or window, in which the blood pressure can vary without operation of the alarm. If the blood pressure monitored by transducer 24 exceeds or falls below the limits, an alarm occurs.

The output voltage developed by pressure variation selection circuit 70 is coupled to a second input of summing circuit 32 and, through an inversion amplifier 72, to the second input of summing circuit 34. Because of the relative polarities of the pressure voltage and of the pressure variation selection voltage, the voltages coupled to summing circuit 34 are subtracted, inverted and the resultant summed inverted voltage is coupled to the plus input of comparator 62. The voltages coupled to the summing circuit 32 are added, inverted and the resultant summed inverted voltage is coupled to the negative input of comparator 60.

If the pressure sensed by pressure transducer 24 increases, the voltage coupled to summing circuit 34 increases, becoming more positive and causing the voltage coupled to the positive input of comparator 62 to become negative. When the pressure sensed by pressure transducer 24 exceeds the limit selected in pressure variation selection circuit 70, the voltage coupled to the positive input of comparator 62 falls below the analog memory voltage coupled from memory circuit 30 to the negative input of comparator 62, causing comparator 62 to develop a low state signal at its output. The low state signal developed by comparator 62 is coupled to one input of a NAND gate 74 which operates in response to the received low state signal to develop a high state signal at its output. An alarm circuit 76 is connected to the output of NAND gate 74 and operates in response to the received high state signal to provide audible and visual alarms and to inhibit further operation of the blood pump, thereby terminating the blood flow from the patient through the dialysis machine.

If the pressure sensed by pressure transducer 24 decreases, indicating a possible leak or break in the line between the patient and the machine or a possible patient problem, the pressure voltage coupled to summing circuit 32 decreases. This produces an increase in the resultant voltage developed by summing circuit 32. Consequently, the voltage coupled to the negative input of comparator 60 becomes more positive. When the pressure sensed by pressure transducer 24 decreases below the lower limit of the pressure variation window selected in pressure variation selection circuit 70, the summed voltage developed by summing circuit 32 and coupled to the negative input of comparator 60 rises above the analog memory voltage coupled to the positive input of comparator 60 and causes comparator 60 to develop a low state signal at its output. The low state signal is coupled to a second input of NAND gate 74, which operates in response to the low state signal to develop a high state signal at its output. The high state signal is coupled to alarm circuit 76 actuating the alarm and deactivating the blood pump.

Protection circuit 78 monitors the output of low pass filter 28, the contents of up/down counter 52, and the level of the power supply for the machine. If the amplified pressure voltage developed at the output of low pass filter 28 exceeds a particular value, corresponding to the value indicating the maximum or full-range reading of pressure transducer 24, protection circuit 78 will develop a signal which is coupled to alarm circuit 76 causing operation thereof. If counter 52 develops a count therein one less than the full capacity of the counter, the counter has reached an unacceptable or overflow condition. Protection circuit 78 operates in response to this count to couple a signal to alarm circuit 76 causing activation thereof. If the power supply to the dialysis machine drops below a specific level for a particular time period, this power loss is detected by protection circuit 78 which develops a signal that is coupled to alarm circuit 76 for activation thereof. If either a power loss condition occurs or a memory overload condition occurs which causes operation of protection circuit 78, the dialysis machine cannot be operated in a normal mode until such time as protection circuit 78 is reset by proper sequential operation of switch 46.

Figure 4:
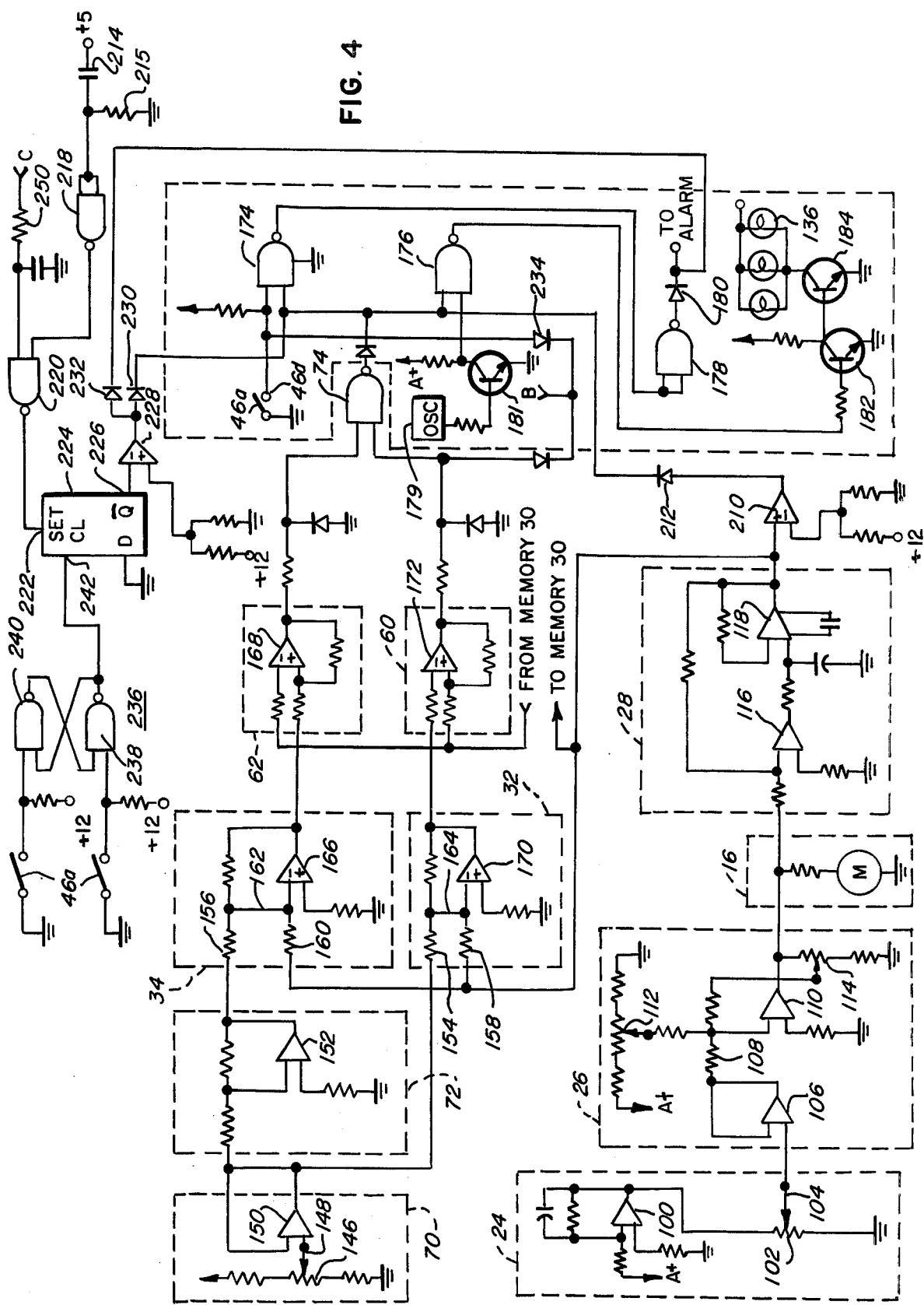
FIG. 4 is a schematic diagram of a portion of the alarm circuit represented in block diagram form in FIG. 3.

Referring now to FIG. 4, pressure transducer 24 includes a constant voltage generator 100 coupled to a potentiometer 102. The potentiometer 102 is connected to an arterial blood line in dialysis machine 10 by way of a pressure sensitive diaphragm connected to arm 104 of potentiometer 102. Changes in pressure cause movement of arm 104. With a constant voltage supplied to potentiometer 102 by constant voltage generator 100, the movement of potentiometer arm 104 causes a change in the voltage level coupled to a buffer amplifier 106 in amplifier and calibration adjusting circuit 26.

Buffer amplifier 106 acts to isolate potentiometer 102 from the following circuitry, and couples the voltage signal received through resistor 108 to a gain control and offset control amplifier 110. Potentiometer 112 and potentiometer 114, connected to gain control and offset control amplifier 110, allow adjustment of the circuit for a proper zero and full scale. These potentiometers and gain control amplifier 110 are set by first applying a pressure corresponding to a minimum reading on meter 16 to potentiometer 102 so that a minimum or zero voltage signal is coupled to and through buffer amplifier 106. Potentiometer 112 then is set so that meter 16 indicates zero on the scale. Then the maximum pressure represented on meter 16 is applied to pressure transducer 24 so that potentiometer 102 couples the maximum desired voltage signal to and through buffer amplifer 106 to gain control and offset control amplifier 110. With maximum pressure applied, potentiometer 114 is adjusted so that meter 16 provides a full scale indication.

In normal operation, when pressure transducer 24 is attached to the blood line, the voltage signal developed at the output of amplifier 110 is somewhere between the voltage limits corresponding to the minimum and maximum meter reading set by potentiometers 112 and 114. This voltage signal is coupled to meter 16 for visual presentation and to and through low pass filter 28. Low pass filter 28 includes a first amplifier 116 which receives the voltage signal from amplifier 110, and a second amplifier 118 whose input is coupled to the output of amplifier 116. Amplifiers 116 and 118 are interconnected in a typical low pass filter configuration and operate as previously described to eliminate extraneous high frequency components. The filtered signal passed by low pass filter 28 is coupled to memory circuit 30, shown in greater detail in FIG. 4A, and to summing circuits 32 and 34.

Figure 4A:
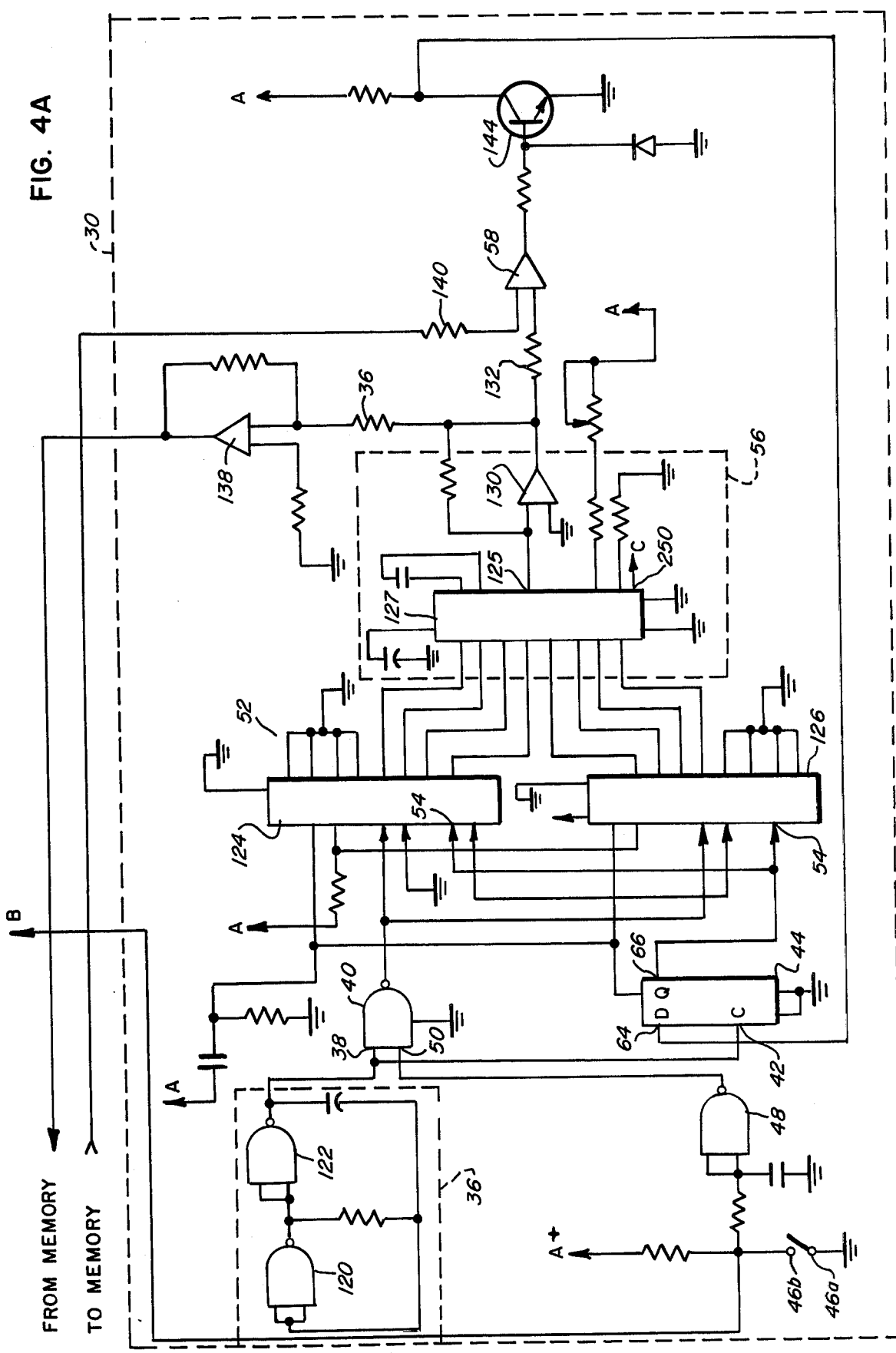
FIG. 4A is a schematic diagram of a second portion of the alarm circuit in FIG. 3.

Referring to FIG. 4A, NAND gates 120 and 122 are interconnected to form oscillator 36 in memory 30. The clock pulses developed by oscillator 36 are coupled from the output of NAND gate 122 to input 38 of NAND gate 40 and to the clock input 42 of flip/flop 44.

Inverter 48, shown in FIG. 3, is shown in FIG. 4A as a two-input NAND gate with both inputs connected together. When switch 46 is in the operate position, a high state signal is coupled to the inputs of NAND gate 48 so that a low state signal is developed at its output and coupled to second input 50 of NAND gate 40. With a low state signal at second input 50 of NAND gate 40, it develops and maintains a high state signal at its output, notwithstanding the clock pulses coupled from oscillator 36 to first input 38. When switch 46 is moved to the set-up position, a high state signal is coupled to input 50 of NAND gate 40. With a high state signal appearing at second input 50, the output of NAND gate 40 will switch between a high and low state signal in response to each clock pulse, thus developing clock pulses that correspond to the clock pulses coupled from oscillator 36. The clock pulses developed at the output of NAND gate 40 are coupled to the clock inputs of first and second counter portions 124 and 126 in up/down counter 52.

Each first and second counter portions 124 and 126 is a four-stage COS/MOS presettable up/down counter, such as is available from the RCA Solid State Division under the part number CD4029AE. Each counter portion will count up or down in accordance with the signal at its control input, and is capable of counting up to $2^4-1$ and down to zero. When first and second counter portions 124 and 126 are connected serially, as shown, they are capable of counting from zero to $2^8-1$. The count is stored in the first and second counter portions 124 and 126 as a digital number in the form of a series of ones and zeros, and it is this series of digits which is coupled in parallel from first and second counter portions 124 and 126 to converter 127 in D/A converter 56.

Converter 127 may, for example, be an eightbit multiplying digital to analog converter, such as is available from Motorola Semiconductor Product, Inc., under the part number MC14081-8. Converter 127 receives the binary number from counter 52 and converts the binary number to an analog current whose amplitude is proportional to the received binary number. This analog current is coupled from output 128 of converter 127 to a current to voltage converter 130.

Current to voltage converter 130 develops an output voltage whose amplitude corresponds to the amplitude of the current received from output 128 of converter 127, so that it is the analog equivalent of the digital number stored in counter 52. The analog memory voltage developed at the output of converter 130 is coupled from D/A converter 56, through resistor 132 to an input of comparator 58, and through resistor 136 to inverter 138. Inverter 138 inverts the received voltage and develops a corresponding voltage inverted in sign at its output. In the preferred embodiment, the voltage developed at the output of inverter 138 is a negative voltage. This voltage is coupled to comparators 60 and 62 shown in FIGS. 3 and 4.

The output of low pass filter 28 coupled to memory 30 is coupled through resistor 140 to one input of comparator 58, and as noted, the analog memory voltage is coupled through resistor 132 to the second input of comparator 58. These two voltages are compared in comparator 58. If the voltage coupled through resistor 140 exceeds the voltage coupled through resistor 132, the output of comparator 58 is a low state signal. This low state signal is inverted by a level shifting transistor 144 in comparator 58 and coupled to the D input 64 of flip/flop 44. Upon receipt of the following clock pulse, a high state signal is developed at the Q output 66 and coupled to control input 54 of counter portions 124 and 126, causing them to count up or add in response to each clock pulse.

When the voltage coupled through resistor 132 exceeds the voltage coupled through resistor 140, comparator 58 develops a high state signal at its output. This high state signal is inverted by level shifting transistor 144 and coupled to the D input 64 of flip/flop 44, and upon receipt of the next following clock pulse flip/flop 44 changes states and develops a low state signal at Q output 66. The low state signal is coupled to control input 54 of counter portions 124 and 126, causing these portions to count down or subtract in response to each clock pulse. Further details of the memory operation have been described previously.

Referring again to FIG. 4, pressure variation selection circuit 70 includes a potentiometer 146 coupled between supply potential and ground potential. Slide control 18, shown on FIGS. 1 and 2, is connected to arm 148 of potentiometer 146 and allows selection of the desired upper and lower limit voltage as previously described. The voltage selected is coupled through arm 148, through a buffer amplifier 150 to amplifier 152 in inversion amplifier 72, and to the summing resistor 154 in summing circuit 32. Amplifier 152 inverts the received voltage and couples the inverted voltage to resistor 156 in summing circuit 34.

The pressure voltage developed at the output of low pass filter 28 is coupled to summing resistor 158 in summing circuit 32 and to summing resistor 160 in summing circuit 34. Resistors 156 and 160 are connected together at summing junction 162 and summing resistors 154 and 158 are connected together at summing junction 164. The voltages coupled to summing resistors 156 and 160 are summed at summing junction 162, and this summed voltage is amplified and inverted by amplifier 166 and coupled to the positive input of comparison amplifier 168 in comparator 62. The voltages coupled to summing resistors 154 and 158 are summed at summing junction 164, and the summed voltage is amplified and inverted by amplifier 170 and coupled to the negative input of comparison amplifier 172 in comparator 60.

The analog memory voltage developed by memory circuit 30 is coupled to the negative input of comparison amplifier 168 and the positive input of comparison amplifier 172. The operation of comparison amplifiers 168 and 172 has been described previously with respect to comparators 60 and 62 in FIG. 3.

The outputs of comparators 60 and 62 are coupled to NAND gate 74, and the output of NAND gate 74 is coupled to one input of NAND gates 174 and 176. An oscillator 179 is coupled through a switching transistor 181 to a second input of NAND gate 176 and switch 46 is connected to the second input of NAND gate 174. A source of voltage is also connected to the second input of NAND gate 174.

As previously explained, if the pressure sensed either exceeds or falls below the windows established by the level set in pressure variation selection circuit 70, one of the comparators 60 or 62 develops a low state signal at its output which is coupled to NAND gate 74. If a low state signal is presented at either input to NAND gate 74, it develops a high state signal at its output which is coupled to one input of NAND gates 174 and 176. In normal operation when a high state signal is coupled to NAND gate 174 from NAND gate 74, the output of NAND gate 174 switches from a high state signal to a low state signal. Inverter 178 inverts this signal to that a high state signal is developed at the output of inverter 178 and coupled through diode 180 to any type of audible alarm desired so that an audible indication of a malfunction is provided. The output also is coupled to the blood pump in order to stop further operation thereof.

Switch 46 can be moved to an override position, this position being shown clearly in FIG. 2. When in the override position, switch arm 46a couples a low state signal from terminal 46d to the second input of NAND gate 174, forcing the output thereof to change to and maintain a high state signal as long as switch 46 is maintained in the override position. With the high state signal developed at the output of NAND gate 174, a low state signal is developed at the output of inverter 178 and coupled through diode 180 to the alarm and pump. The presence of a low state signal will terminate the audible alarm and allow continued operation of the pump, thus allowing continued blood pumping during investigation of the cause of pressure change and preventing unnecessary shock to the patient. It should be noted that the override function only is operative in the absence of an alarm signal from protection circuit 78.

The high state signal developed at the output of NAND gate 74 in response to exceeding or falling below the window limits established by pressure variation selection circuit 70 is also coupled to one input of NAND gate 176. The clock pulses from oscillator 179, are coupled through switching transistor 181 to the second input of NAND gate 176, causing NAND gate 176 to switch states changing from high to low state signals at its output at the clock pulse rate. Switching at the output of the NAND gate 176 will cause transistors 182 and 184 to switch at a corresponding rate. Light bulbs 186 connected to transistor 184 will be turned on and off at the clock rate by the switching of transistor 184, thus providing an additional indication of the alarm condition.

The output of low pass filter 28 is also coupled to the positive input of a comparator 210 in protection circuit 78. The negative input of comparator 210 receives a fixed voltage thereat which corresponds to the voltage resulting from a full range pressure signal to the pressure signal. Should the voltage coupled to the positive input of comparator 210 exceed the voltage at the negative input thereof, thus indicating receipt of a pressure signal which causes in excess of full-scale deflection at meter 16, the output of comparator 210 will change from a zero or low state signal to a high state signal. This high state signal is coupled through diode 212 to the output of NAND gate 74 and the first input of NAND gates 174 and 176. As previously explained, the high state signal at the first input of NAND gate 174 causes operation of the audible alarm and terminates further operation of the blood pump. In like manner, the high state signal will cause NAND gate 176 to switch states. This will cause light bulbs 186 to turn off and on at the clock rate, thus providing visual indication of the meter overrange condition.

Should a power reduction condition occur whereby the power is reduced below a level of, for example two-and-one-half (2.5) volts for a specific time period, capacitor 214 in protection circuit 78 will begin to discharge. When power is again returned to its normal level, such as for example when the equipment is turned on, capacitor 214 will recharge momentarily developing a high state signal at the junction between capacitor 214 and resistor 215. This high state signal is coupled to both inputs of NAND gate 218 causing the output thereof to switch from a high state to a low state. The output of NAND gate 218 is coupled to one input of NAND gate 220. When a low state signal is presented at the input of NAND gate 220, it develops a high state signal at its output which is coupled to the set input 222 of "D" type flip/flop 224. A high state signal at set input 222 of flip/flop 224 will cause flip/flop 224 to set and develop a zero or low state signal at the Q output 226. This low state signal is coupled to the negative input of comparator 228, the positive input thereof being coupled to the junction of a resistive divider.

Comparator 228 will change states in response to the zero or low state signal at its negative input and develop a high state signal at its output. This high state signal is coupled through diode 230 to one input of NAND gates 174 and 176 causing operation thereof and the resulting visual alarm as previously explained. The high state signal developed at the ouput of comparator 228 is also coupled through diode 232 directly to the output of diode 180, thus actuating the audible alarm and shutting off the blood pump. This connection is provided in order to insure an audible alarm while the machine is in the set-up mode, such alarm otherwise being inhibited by the presence of diode 234.

Once flip/flop 224 sets, both the visual and audible alarms will continue until flip/flop 224 is reset. Reset only can occur by operation of the toggle flip/flop circuit 236 in protection circuit 78. To operate toggle circuit 236, switch 46 is moved from the set-up to the operate position and then back to the set-up position. When switch 46 is in the set-up position, a ground potential is coupled to one input of NAND gate 238 in toggle 236. When switch 46 is in the operate position, a ground potential is coupled to one input of NAND gate 240 in toggle 236. When the ground potential coupled to the input of NAND gate 238 is removed by movement of switch 46 from the set-up position back to the operate position, toggle 236 changes states and develops a zero or low state signal at its output. When switch 46 is again moved from the operate back to the set-up position, the ground potential at one input of NAND gate 240 is removed and a positive potential is applied to that input. The positive potential causes toggle 236 to change states and develop a one or high state signal at its output.

The output of toggle 236 is coupled to the clock input 242 of flip/flop 224. When the output of toggle 236 changes from a low to a high state signal, this change is coupled to clock input 242 causing the output 226 to change from a low to a high state signal. This high state signal is coupled to the negative input of comparator 228. With a high state signal at the negative input of comparator 228, it will develop a low state signal at its ouput. The low state signal is coupled to NAND gates 174 and 176 and will terminate the audible and visual alarms.

First and second counter portions 124 and 126, shown in FIG. 4A, are capable of counting from zero to $2^8 - 1$. If a count of $2^8$ minus 1 is developed in first and second counter portions 124 and 126, thus indicating a pressure voltage at the maximum limits of the counter capacity, a low state signal will be developed at output 248 of second counter portion 126 in FIG. 4A. This low state signal is coupled through resistor 250, shown in FIG. 4, which is part of protection circuit 78. The zero or low state signal is coupled to a second input of NAND gate 220 causing NAND gate 220 to develop a high state signal at its output in the same manner as described before for receipt of a low state signal at its first input. This high state signal is coupled to the set input 222 of flip/flop 224 as previously described. The sequence of operation for the remaining circuitry is the same as previously described and will result in visual and audible alarms, thus indicating a memory overload condition which must be rectified. The reset and termination of this alarm is as previously explained with regard to the reset of the protection circuit upon restoration of power.

Figure 5:
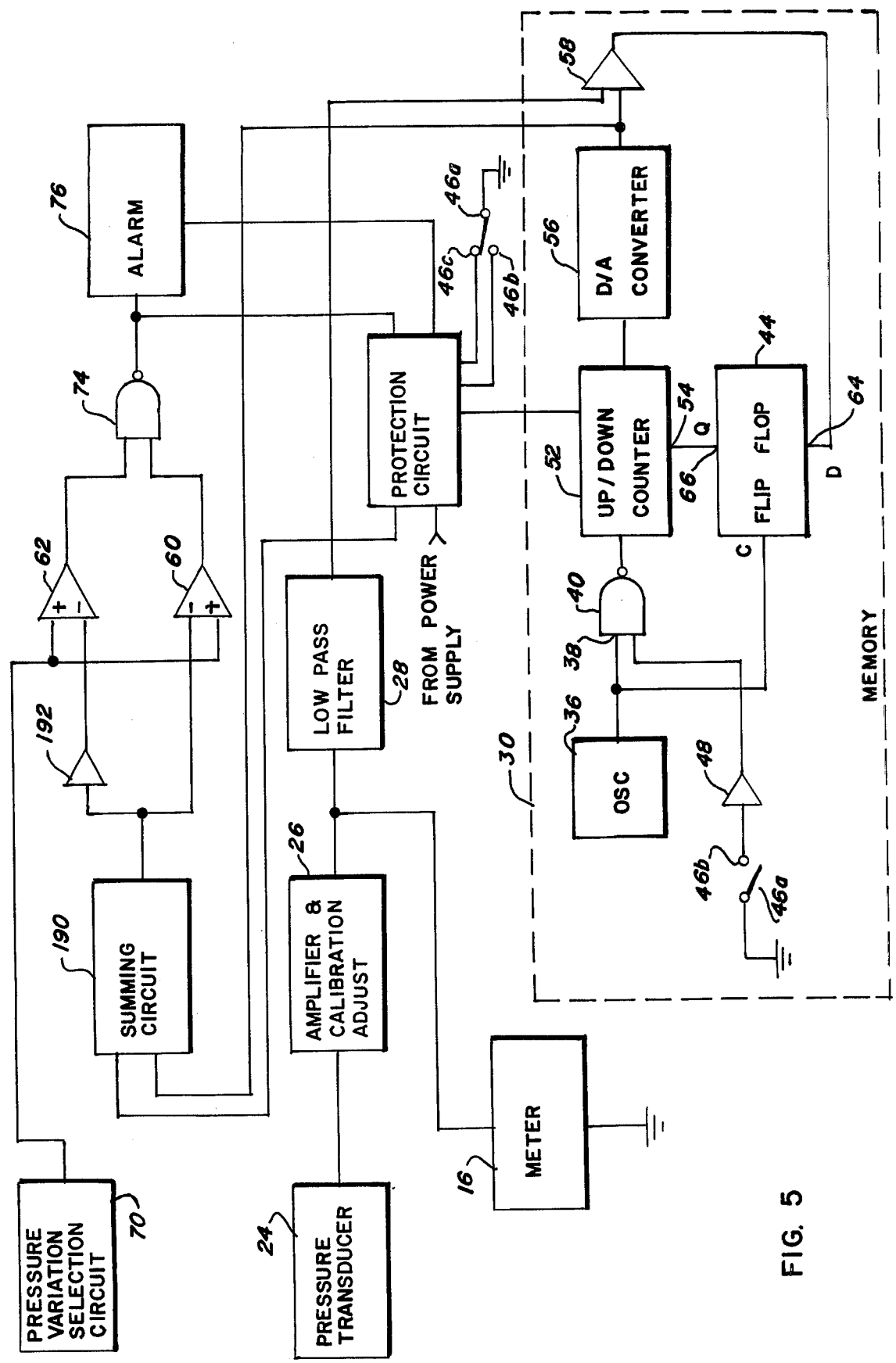
FIG. 5 is a block diagram of another embodiment of the alarm circuit of this invention.

Referring now to FIG. 5, a second embodiment of the alarm circuit of the invention is shown. A number of elements in the first and second embodiments of this invention are the same. Those elements which are the same have been identified with common numbers, and as they have previously been described with respect to FIGS. 3 and 4, will not be described again.

The analog memory voltage developed by memory 30 in this embodiment is coupled to one input of summing circuit 190, and the pressure voltage developed at the output of low pass filter 28 is coupled to the second input of summing circuit 190. Summing circuit 190 sums the two voltages together and couples a summed inverted voltage to the negative input of comparator 60 and through inverter 192 to the negative input of comparator 62. The output of pressure variation selection circuit in this embodiment is coupled to the positive input of comparator 62 and the positive input of comparator 60.

The voltage coupled from digital memory 30 is a negative voltage, and the voltage coupled from low pass filter 28 is a positive voltage, so that these voltages are subtracted from one another in summing circuit 190. If the pressure sensed by the pressure transducer 24 decreases, the voltage coupled from low pass filter 28 to summing circuit 190 will decrease resulting in a positive increase in the summed voltage coupled through summing circuit 190 to the negative input of comparator 60. When the voltage coupled to the negative input increases above the voltage coupled from pressure variation selection circuit 70 to the positive input of comparator 60, comparator 60 changes states and develops a low state signal at its output, causing NAND gate 74 to change states and develop a high state signal at its output for operating the alarm 76.

If the pressure sensed by pressure transducer 24 increases, the voltage coupled to summing circuit 190 increases, causing a negative increase in the voltage developed at the output of summing circuit 190. The negative increasing voltage is inverted by inverter 192, and the positive increasing voltage is coupled to the negative input of comparator 62. When the voltage coupled to the negative input of comparator 62 increases above the voltage coupled from pressure variation selection circuit 70 to the positive input of comparator 62, thus indicating a rise in pressure above the upper pressure limit, comparator 62 changes states and develops a low state signal at its output which is coupled to NAND gate 74. This low state signal causes the NAND gate 74 to change states and develop a high state signal at its output for operating alarm circuit 76.

Figure 6:
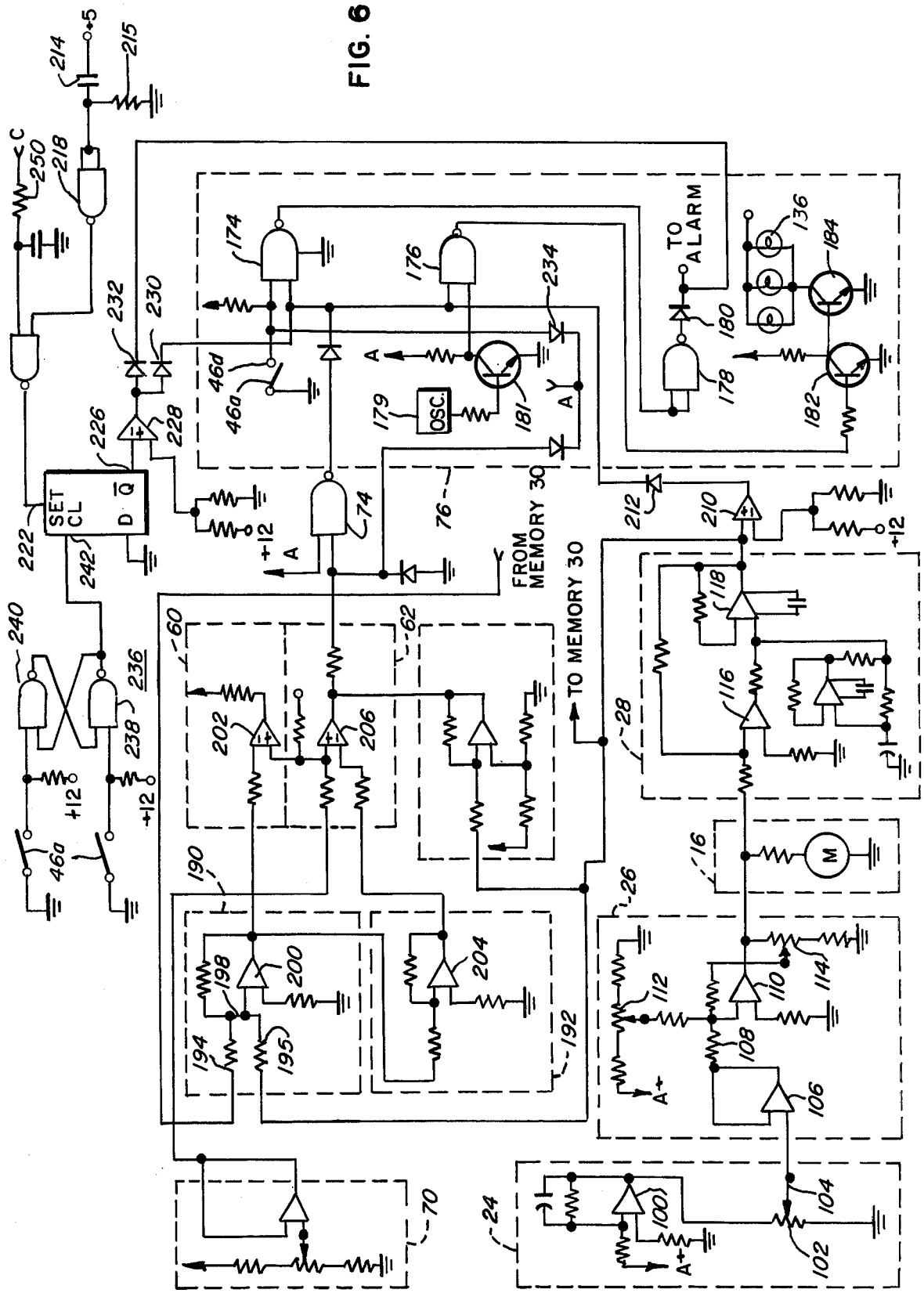
FIG. 6 is a schematic diagram of a portion of the alarm circuit represented in block diagram form in FIG. 5.

Referring now to FIG. 6, the inverted output of memory circuit 30 is coupled to summing resistor 194 in summing circuit 190, and the pressure voltage at the output of low pass filter 28 is coupled to summing resistor 196. The two voltages are summed at summing junction 198, and the summed voltage is inverted by amplifier 200 and coupled to one input of comparison amplifier 202 in comparator 60. The output of amplifier 200 is also coupled to amplifier 204 in inverter 192; the output of amplifier 204 in inverter 192 is coupled to one input of comparison amplifier 206 in comparator 62. In this embodiment the outputs of comparison amplifiers 202 and 206 are connected together and to one input of NAND gate 74, however, the operation is the same as previously described.

While the present invention has been described by reference to specific examples, it is to be understood that modifications may be made by those skilled in the art without actually departing from the invention shown and described herein. It is therefore intended that the appended claims cover all variations that fall within the scope and spirit of this invention.

What is claimed is:

1. In a dialysis machine capable of at least one type of malfunction an alarm means operative in response to particular blood pressure changes to operate, said alarm means including in combination:
   blood pressure sensing means operative to develop a pressure signal which varies in accordance with blood pressure;
   memory means operative to receive said pressure signal, said memory means including storage means for storing said received pressure signal and means for developing a memory signal in response to said storage signal, said memory means storage means only storing received pressure signals below a particular value;
   control circuit means coupled to said blood pressure sensing means and said memory means and operative in response to at least a first particular difference between said memory signal and said pressure signal to operate for providing an alarm; and
   protection circuit means including gating circuit means coupled to said memory means and operative in response to a pressure signal received therein in excess of said particular value to operate for providing said alarm.

2. The dialysis machine of claim 1, wherein power from a source of power is applied thereto, and said received pressure signal stored in said memory means storage means is released therefrom upon a particular reduction of power for a first time period, said protection circuit means gating circuit means being coupled to said source of power and responsive to said particular reduction of power for first said time period and return thereof to operate for providing said alarm.

3. The dialysis machine of claim 2, wherein said gating circuit means includes a first gate operative in response to said power reduction for said first time period and restitution thereof to develop a first gate signal, bistable means coupled to said first gate and operative in response to said first gate signal to develop a first bistable signal for providing said alarm.

4. The dialysis machine of claim 3, wherein said gating circuit means includes second bistable means coupled to said first bistable means and selectively operative to reset said first bistable means, terminating said first bistable signal.

5. The dialysis machine of claim 4, wherein said second bistable means includes switch means having at least a first and second position, a toggle circuit coupled to said switch means and operative in response to said switch means movement to said first position to develop a first toggle signal and said switch means movement to said second position to develop a second toggle signal, said first bistable means operative in response to said second toggle signal to reset and terminate said first bistable signal.

6. The dialysis machine of claim 3, wherein said first gate is operative in response to a pressure signal in said memory in excess of said particular value to develop said first gate signal, said bistable means operative in response to said first gate signal to develop said first bistable signal for providing said alarm.

7. The dialysis machine of claim 1, wherein said blood pressure sensing means develops a blood pressure signal having a first value, said protection circuit means including comparison means coupled to said blood pressure sensing means and operative in response to a blood pressure signal of first value to operate for providing an alarm.

8. The dialysis machine of claim 7, wherein said blood pressure sensing means includes a pressure transducer operative to sense blood pressure below a first level, said pressure sensing means developing said pressure signal having a first value substantially in response to a blood pressure of said first level.

9. The dialysis machine of claim 7, wherein said blood pressure sensing means includes a pressure transducer for developing a pressure signal which varies in accordance with blood pressure, level adjustment means coupled to said pressure transducer for adjusting a maximum pressure signal, meter means coupled to said level adjustment means and operative in response to said blood pressure signal to provide a visual indication of said blood pressure, said meter means having a maximum pressure limit thereon corresponding to a blood pressure signal having a second value less than said first value whereby said comparison means operates to provide said alarm in response to a blood pressure in excess of said meter means maximum pressure limit.

10. In a dialysis machine wherein power from a source of power is applied thereto, an alarm means operative in response to blood pressure changes to operate, said alarm means including in combination:
   blood pressure sensing means operative to develop a pressure signal which varies in accordance with blood pressure; said blood pressure sensing means operative to develop a blood pressure signal having a first value, memory means operative to receive said pressure signal, said memory means including storage means for storing said received pressure signal in digital form as a digital signal and means coupled to said storage means and operative in response to said stored digital signal to develop a memory signal; said received pressure signal stored in said storage means being released therefrom upon a particular reduction in power for a first time period and said storage means only storing received pressure signals below a particular value;
   pressure variation selection means operative to develop a variation signal representing blood pressure variation limits;
   comparison means coupled to said sensing means, memory means and pressure variation selection means and operative in response to said pressure signal greater than said memory signal plus said variation signal to develop a first comparison signal and operative in response to said pressure signal less than said memory signal minus said variation signal to develop said first comparison signal;
   control circuit means coupled to said comparison means and operative in response to said first comparison signal to operate for providing an alarm;
   gating circuit means coupled to said source of power and operative in response to said reduction of power for said first time period and restoration thereof to operate for providing said alarm; said gating circuit means responsive to a pressure signal received at said memory storage means in excess of said particular value to operate for providing said alarm; and second comparison means coupled to said blood pressure sensing means and responsive to a blood pressure signal of said first value to operate for providing an alarm.

11. In a dialysis machine capable of at least one type of malfunction an alarm means operative in response to particular blood pressure changes to operate, said alarm means including in combination:

blood pressure sensing means operative to develop a pressure signal which varies in accordance with blood pressure;

memory means operative to receive said pressure signal, said memory means including storage means for storing said received pressure signal and means for developing a memory signal in response to said storage signal, said memory means storage means only storing received pressure signals below a particular value;

control circuit means coupled to said blood pressure sensing means and said memory means and operative in response to at least a first particular difference between said memory signal and said pressure signal to operate for providing an alarm; and protection circuit means including a first gate, coupled to said memory means and operative in response to a pressure signal received therein in excess of said particular value to develop a first gate signal, bistable means coupled to said first gate and operative in response to said first gate signal to develop a first bistable signal for providing said alarm.

12. The dialysis machine of claim 11, wherein said gating circuit means includes second bistable means coupled to said first bistable means and selectively operative to reset said first bistable means terminating said first bistable signal.

13. The dialysis machine of claim 12, wherein said second bistable means includes switch means having at least a first and second position, a toggle circuit coupled to said switch means and operative in response to said switch means movement to said first position to develop a first toggle signal and switch means movement to said second position to develop a second toggle signal, said first bistable means operative in response to said second toggle signal to reset and terminate said first bistable signal.

14. The dialysis machine of claim 12, wherein power from a source of power is applied thereto and said received pressure signal stored in said memory means storage means is released therefrom upon a particular reduction of said power for the first time period, said protection circuit means including a second gate coupled to said source of power and to said first gate and operative in response to removal of said power for a particular time period and restitution thereof to develop a second gate signal, said first gate operative in response to said second gate signal to develop said first gate signal for providing said alarm.

15. In a dialysis machine capable of at least one type of malfunction an alarm means operative in response to particular blood pressure changes to operate, said alarm means including in combination:

blood pressure sensing means operative to develop a pressure signal which varies in accordance with blood pressure;

Memory means operative to receive said pressure signal, said memory means including storage means for storing said received pressure signal and means for developing a memory signal in response to said storage signal, said memory means having power from a source of power applied thereto and said received pressure signal stored in said memory means storage means being released therefrom upon a particular reduction of power for a first time period, said memory means storage means being operative to store only said received pressure signals below a particular value;

control circuit means coupled to said blood pressure sensing means and said memory means and operative in response to at least a first particular difference said memory signal and said pressure signal to operate for providing an alarm; and protection circuit means including gating circuit means having a first gate coupled to said source of power and operative in response to said particular reduction of power for said first period of time and restitution thereof to develop a first gate signal, bistable means coupled to said first gate and operative in response to said first gate signal to develop a first bistable signal for providing said alarm, said first gate being further operative in response to a pressure signal in said memory in excess of said particular value to develop said first gate signal, said bistable means operative in response to said first gate signal to develop said first bistable signal for providing said alarm.

* * * * *